(12) United States Patent  
Gutman et al.

(10) Patent No.: US 7,026,483 B2  
(45) Date of Patent: Apr. 11, 2006

(54) FORMS OF CABERGOLINE

(75) Inventors: Arie Gutman, Haifa (IL); Boris Tishin, Haifa (IL); Alex Vilenski, Haifa (IL); Albay Agazade, Kirist Motzskin (IL); Boris Pertzikov, Haifa (IL); Gennady Nisnevich, Haifa (IL)

(73) Assignee: Finetech Laboratories, Ltd., Haifa (IL)

( * ) Notice: Subject to any disclaimer, the term of this patent is extended or adjusted under 35 U.S.C. 154(b) by 0 days.

(21) Appl. No.: 10/827,955

(22) Filed: Apr. 20, 2004

(65) Prior Publication Data

US 2004/0209910 A1 Oct. 21, 2004

(30) Foreign Application Priority Data

Apr. 21, 2003 (IL) .................................. 155545/2

(51) Int. Cl.
*C07D 457/06* (2006.01)
*A61K 31/48* (2006.01)

(52) U.S. Cl. ........................... 546/69; 514/288; 546/67

(58) Field of Classification Search ................ 514/288; 546/69, 67
See application file for complete search history.

(56) References Cited

U.S. PATENT DOCUMENTS

| 4,526,892 A | 7/1985 | Salvati et al. |
| 5,382,669 A | 1/1995 | Candiani et al. |
| 6,673,806 B1 | 1/2004 | Tomasi et al. |
| 6,680,327 B1 | 1/2004 | Candiani et al. |
| 6,696,568 B1 | 2/2004 | Gutman et al. |

| 2002/0123503 A1 | 9/2002 | Ross et al. |
| 2003/0149067 A1 | 8/2003 | Tomasi et al. |

FOREIGN PATENT DOCUMENTS

| GB | 2103603 | 2/1983 |
| WO | WO 01/70740 | 9/2001 |
| WO | WO 03/78392 | 9/2003 |
| WO | WO 03/78433 | 9/2003 |

OTHER PUBLICATIONS

Ashford, S., et al., "A Practical Synthesis of Cabergoline," *J. Org. Chem.*, 67: 7147-50, 2002.
Brambilla, E., et al., "Synthesis and Nidation Inhibitory Activity of a New Class of Ergoline Derivatives," *Eur. J. Med. Chem.*, 24: 421-26, 1989.
Candiani, I., et al., "The Ligand Effect in Copper(I)-Catalyzed Chemoselective Amide Carbamoylation in Cabergoline Synthesis," *Synlett,* 605-06, 1995.
Sabatino, P., et al., "X-ray Crystal Structure and Conformational Analysis of N-(3-Dimetylaminopropyl)-N-(Ethylaminocarbonyl)-6-(2-propenyl)Ergoline-8β-Carboxamide (Cabergoline): Comparison with Bromocriptine and Lisuride and a Hypothesis for its High Dopaminergic Activity," *Il Farmaco,* 50: 175-78, 1995.
Federal Register, 62: 67377-88, 1997.
The Merck Index, 12th Edition, p. 1637, 1996.

*Primary Examiner*—Charanjit S. Aulakh
(74) *Attorney, Agent, or Firm*—Frommer Lawrence & Haug LLP; Marilyn Matthes Brogan

(57) ABSTRACT

The invention provides methods for preparing amorphous physical form of cabergoline, and solvate form A of cabergoline useful in the preparation of the first mentioned physical form. A method for treating a prolactin disorder with medicaments prepared from amorphous physical form of cabergoline and solvate form A of cabergoline is also disclosed.

14 Claims, 8 Drawing Sheets

FORMS OF CABERGOLINE

RELATED APPLICATIONS

This application claims priority from Israeli patent application No. 155545, filed on Apr. 21, 2003, entitled tert-BUTYL METHYL ETHER SOLVATE FORM OF CABERGOLINE. The disclosure of this patent application as well as the references cited therein and the references cited herein are expressly incorporated by reference.

FIELD OF THE INVENTION

Figure 1:
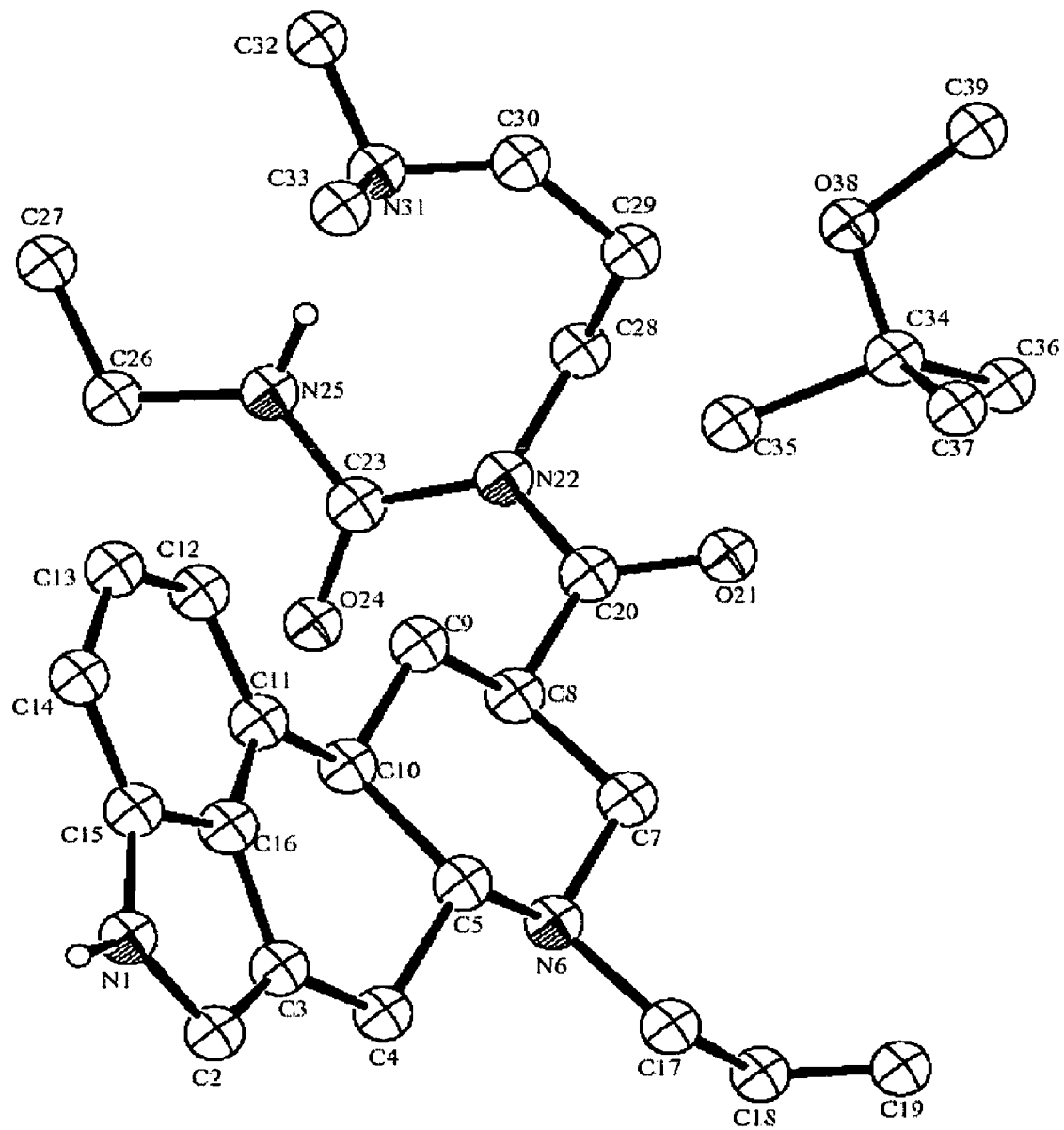
FIG. 1 schematically shows a perspective view of cabergoline and tert-butyl methyl ether molecules and the atomic numbering of non-hydrogen atoms as derived from single crystal x-ray analysis of solvate form A cabergoline. (Atomic coordinates based on Table 2).

This invention relates to a new crystalline form of cabergoline and to processes for its preparation. Uses of the novel form of cabergoline in purification of crude cabergoline, in the preparation of amorphous cabergoline and in the manufacture of a medicament are disclosed. A method for treating a prolactin disorder with the medicaments is also disclosed.

List of References

The following prior publications are considered to be pertinent for the purpose of understanding the background of the present invention:
S. F. Ashford et al., J. Org. Chem., 2002, v. 67, 7147;
E. Brambilla et al., Eur. J. Med. Chem., 1989, v. 24, 421;
I. Candiani et al., Synlett, 1995, 605;
P. Sabatino et al., Farmaco, 1995, v. 50, 175;
Federal Register, 1997, v. 62, 67377–88;
The Merck Index, 12th Edition, 1637;
GB 2,103,603;
U.S. Pat. No. 4,526,892;
U.S. Pat. No. 5,382,669;
U.S. Pat. No. 6,673,806;
U.S. Pat. No. 6,680,327;
U.S. Pat. No. 6,696,568;
US 2002/0123503 A1;
US 2003/0149067 A1;
WO 01/70740;
WO 03/78392 A2;
WO 03/78433 A1.

BACKGROUND OF THE INVENTION

Cabergoline is a long-acting oral dopamine agonist specific for the D2 receptor and is used to treat different types of medical problems that occur when too much of the hormone prolactin is produced. Cabergoline works by stopping the brain from making and releasing the prolactin hormone from the pituitary. It can be used to treat certain menstrual problems, fertility problems in men and women, and pituitary prolactinomas (tumors of the pituitary gland).

Prolactin hypersecretion, or hyperprolactinemia, is a condition characterised by an increased level of prolactin. Hyperprolactinemia may have anyone of a number of functional causes, including various neurogenic causes such as thoracic sensory nerve stimulation, stress, and psychogenic causes, various hypothalamic causes such as diffuse processes, granulomatous diseases, neoplasms, stalk section, empty sella, non-lactotropic cell pituitary tumors, and prostradiation treatment to sella, various pituitary causes such as prolactinomas and pituitary lactotropic cell hyperplasia, and various endocrine causes such as pregnancy, estrogen administration, hypothyroidism, and adrenal insufficiency.

Cabergoline, 1-(6-allylergoline-8β-carbonyl)-1-[3-(dimethylamino)propyl]-3-ethylurea, having the formula:

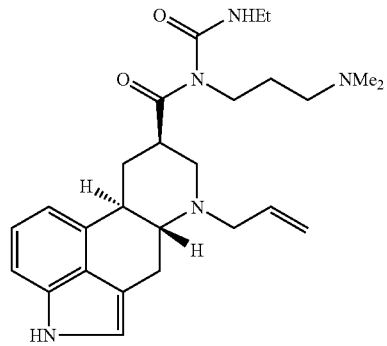

is one of the most potent prolactin inhibitors (Brambilla, 1989 and The Merck Index, 12th Edition, 1637).

Cabergoline may be prepared by the method described in Example 1 of U.S. Pat. No. 6,696,568. Alternatively, cabergoline may be prepared by the methods described by Ashford (2002), Brambilla (1989), Candiani (1995), GB 2,103,603, U.S. Pat. No. 4,526,892 and U.S. Pat. No. 5,382,669.

U.S. Pat. No. 6,673,806, U.S. Pat. No. 6,680,327, US 2003/0149067, WO 03/78392, WO 03/78433 and Sabatino (1995) disclose five physical forms of cabergoline, designated Form I, Form II, Form V, Form VII and Form X. These forms differ from one another in respect of their physical properties, stability, spectral data and methods of preparation. Among these forms, Forms V and X are solvate forms of cabergoline. More precisely, there are toluene solvate forms of cabergoline. Toluene is related to Class 2 solvents. According to Federal Register, 1997, v. 62, 67377–88, the use of Class 2 solvents should be limited in pharmaceutical products because of their inherent toxicity.

Citation or identification of any document in this application is not an admission that such document is available as prior art to the present invention.

SUMMARY OF THE INVENTION

The present invention provides for, inter alia, new solid forms of cabergoline—amorphous cabergoline and tert-butyl methyl ether solvate form A of cabergoline, the latter is referred to as solvate form A of cabergoline. The new forms of cabergoline are relatively stable physical form of cabergoline. Preferably, each of the new forms of cabergoline is substantially free of other physical forms.

The present invention also provides a method of preparing amorphous physical form of cabergoline from crude cabergoline comprising the steps of:
a) mixing cabergoline with tert-butyl methyl ether;
b) isolating the precipitated solid;
c) drying the solid at 0–30° C. to obtain solvate form A of cabergoline substantially free from other physical forms;
d) conversion of the solvate form A of cabergoline to the desired amorphous physical form of cabergoline.

The present invention also provides the use of amorphous physical form of cabergoline and solvate form A of cabergoline in the manufacture of a medicament. The medicament is prepared by combining the physical forms of cabergoline with pharmaceutically acceptable excipients.

The present invention also relates to the field of hyperprolactinemias, and prolactinomas. More specifically, the present invention relates to the treatment of a subject afflicted with either condition, and the lowering of prolactin levels and/or the size of the tumor by administration to the subject by the medicament prepared from solvate form A of cabergoline or amorphous physical form of cabergoline.

DETAILED DESCRIPTION

The present invention discloses, according to a first of its aspects, a new amorphous physical form of cabergoline. Preferably, the amorphous physical form of cabergoline is substantially free of other physical forms. Suitably, amorphous physical form of cabergoline contains not more than 20%, preferably not more than 10% of any crystalline form of cabergoline. Most preferably the amorphous physical form of cabergoline contains not more than 5% of any crystalline form of cabergoline.

Figure 7:
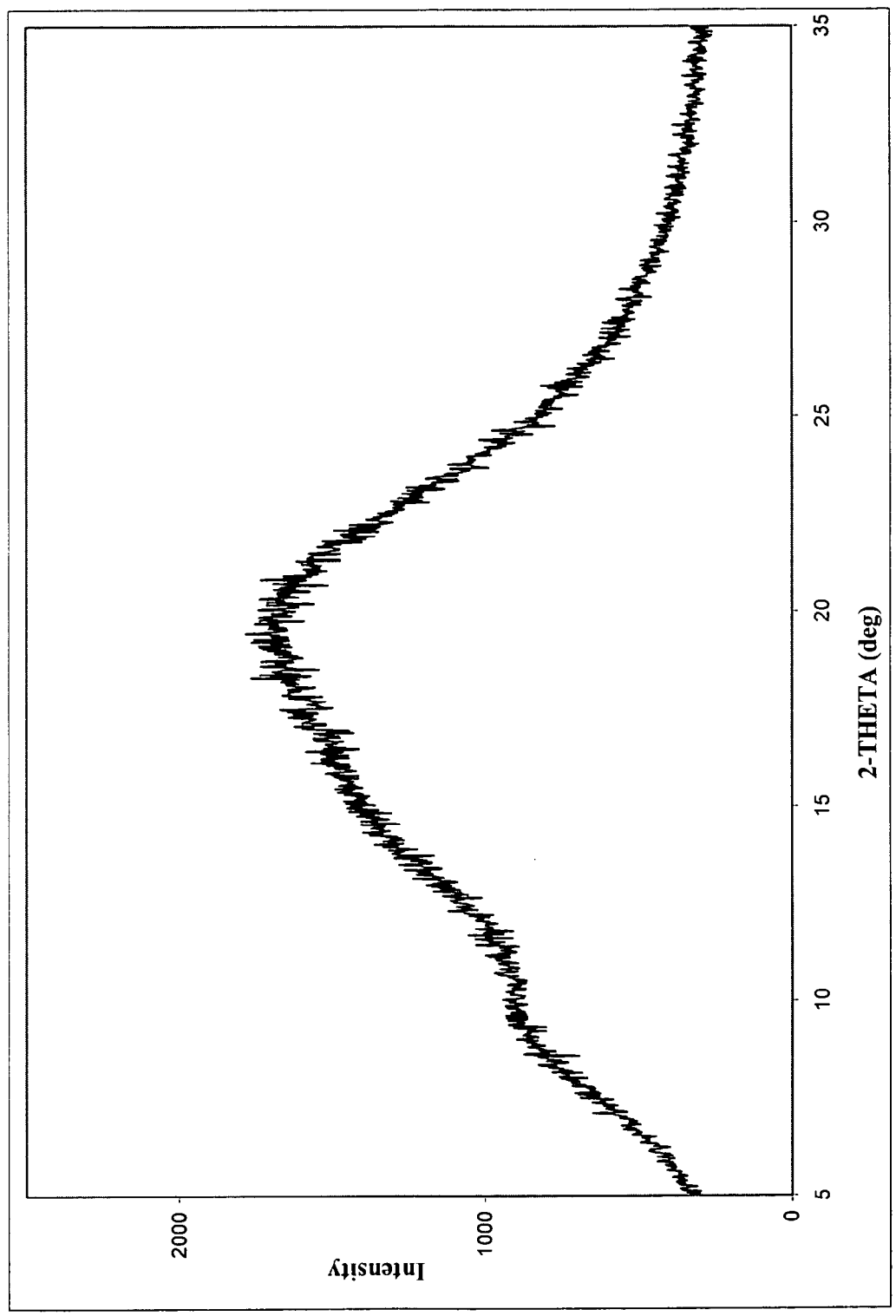
FIG. 7 shows a characteristic x-ray powder diffraction pattern of amorphous physical form of cabergoline. Vertical axis: intensity (CPS); Horizontal axis: 2θ (degrees).

The amorphous physical form of cabergoline has a halo x-ray powder diffraction pattern as depicted in FIG. 7.

Figure 8:
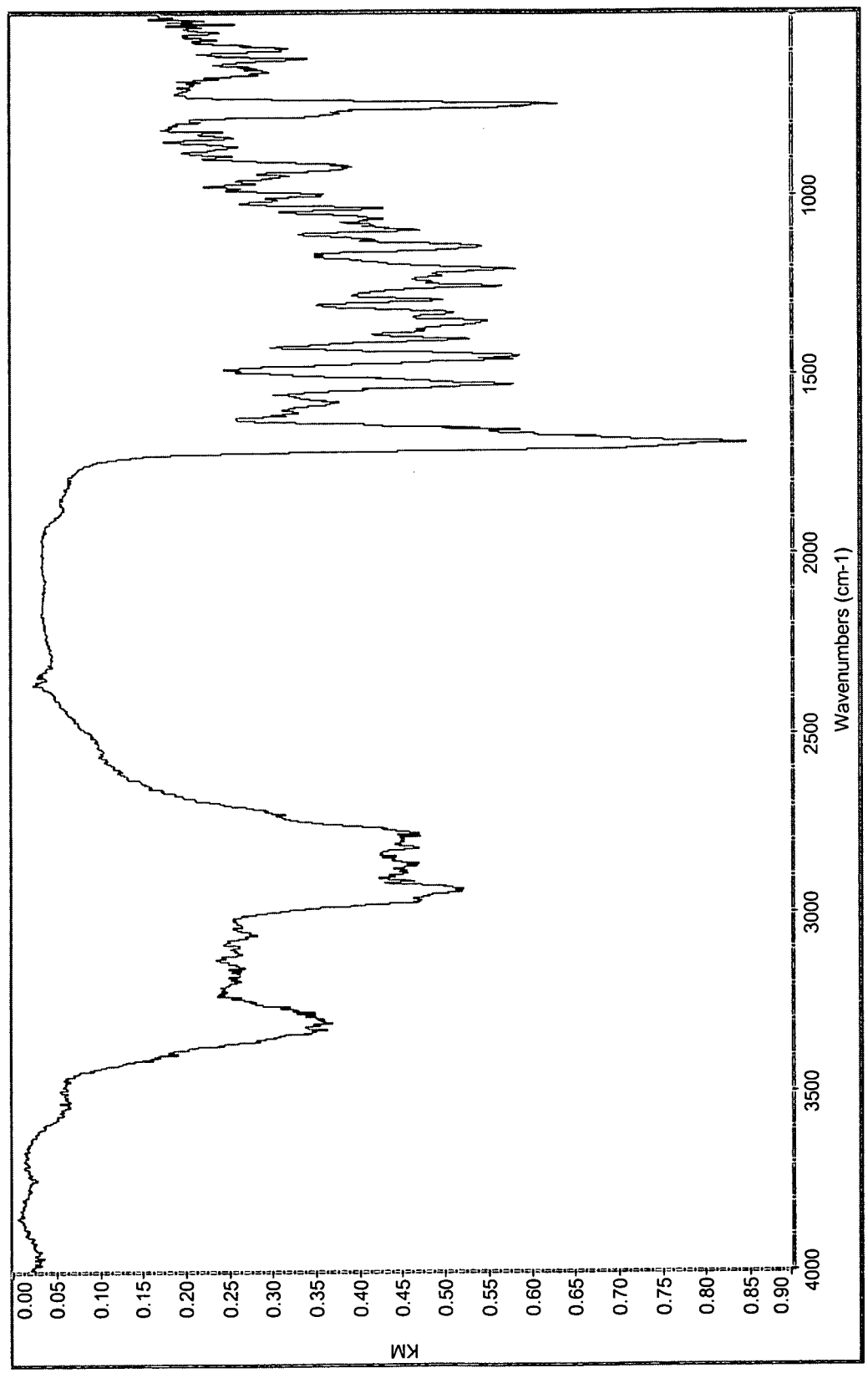
FIG. 8 shows the infrared spectrum (diffuse reflectance, DRIFTS) of amorphous cabergoline in potassium bromide.

The amorphous physical form of cabergoline was further characterized by an infrared absorption spectrum carried out in potassium bromide as depicted in FIG. 8.

The present invention also provides the method of preparing amorphous physical form of cabergoline, which method comprises the preparation of solvate form A of cabergoline and its conversion into amorphous physical form of cabergoline. Preferably, the method comprises the step of:
a) recrystallizing or crystallizing, or triturating or/and reslurring of cabergoline in tert-butyl methyl ether;
b) isolating the precipitated solid;
c) drying the solid at 0–30° C. to obtain solvate form A of cabergoline having x-ray powder diffraction pattern of FIG. 2; and
d) conversion the solvate form of cabergoline into amorphous physical form of cabergoline.

Optionally, the conversion the solvate form of cabergoline into amorphous physical form of cabergoline comprises the steps of:
a) dissolving solvate form A of cabergoline in organic solvent; and
b) evaporating the solution prepared in step (a) to obtain desired solid.

Preferably, said organic solvent is selected from the group consisting of alcohols, ethers, esters and ketones. More preferably, said organic solvent is ethanol, isopropanol, ethyl ether, isopropyl ether, tetrahydrofuran, ethyl acetate, methyl acetate, acetone, and methyl ethyl ketone. Most preferably, the solvent is ethanol or isopropanol.

Preferably, the method of preparing amorphous physical form of cabergoline comprises the step of:
a) dissolving solvate form A of cabergoline in organic solvent;
b) mixing the solution of cabergoline with anti-solvent;
c) evaporating the obtained suspension under reduced pressure at 0–40° C. to obtain desired solid.

More preferably, the method of preparing amorphous physical form of cabergoline, comprising the step of:
a) dissolving solvate form A of cabergoline in an organic solvent;
b) mixing the solution of cabergoline with anti-solvent;
c) isolating of the precipitated solid;
d) drying the solid at 0–40° C. to obtain desired solid.

Preferably, the anti-solvent is saturated hydrocarbon. More preferably, the anti-solvent selected from the group consisting of pentane, heptane, hexane and cyclohexane.

Most preferably, the method of preparing of amorphous physical form of cabergoline comprises the steps of:
a) dissolving solvate form A of cabergoline in a solvent; and
b) lyophilizing the solution prepared in step (a) to obtain desired solid.

Preferably, said solvent is selected from the group consisting of tert-butanol, aqueous tert-butanol, 1,4-dioxane, aqueous 1,4-dioxane, benzene, dimethyl carbonate and cyclohexane.

The present invention also provides the use of amorphous physical form of cabergoline or solvate form A of cabergoline in the manufacture of a medicament. The medicaments prepared from amorphous physical form of cabergoline or solvate form A of cabergoline may be used in a manner similar to that of medicament prepared from any existing forms of cabergoline. Preferably, the medicament is prepared by combining amorphous physical form of cabergoline or solvate form A of cabergoline with pharmaceutically acceptable excipients. Preferably, the excipient may be an acid, a carrier, a binder, a diluent, a lubricant, a glidant, an adjuvant or a combination thereof. More preferably, the suitable pharmaceutically acceptable excipients include the following components:

i) Acids, such as pharmaceutically acceptable organic or inorganic acids, e.g. acetic acid, stearic acid, tartaric acid, citric acid, leucine or a combination thereof;

ii) Binders, such as cellulose and its derivatives, e.g. ethyl cellulose hydroxypropylmethyl cellulose, hydroxypropylcellulose, hydroxyethyl cellulose, sodium carboxymethyl cellulose, starches, polyvinyl pyrrolidone, natural gums, corn syrup, polysaccharides (including acacia, tragacanth, guar, and alginates), gelatin, or a combination thereof;

iii) Glidants, such as talc, fumed silica, or a combination thereof;

iv) Lubricants such as magnesium stearate, calcium stearate, aluminum stearate, stearic acid, calcium oleate, talc, mineral oil, waxes, glyceryl behenate, potassium stearyl fumarate, sodium stearyl fumarate, hydrogenated vegetable oils, or a combination thereof. Such lubricants are commonly included in the final tabletted product in amounts of less than 1% by weight;

v) Diluents, such as lactose, cellulose, starch or calcium phosphate or a combination thereof.

Preferably, the medicament comprises a therapeutically effective amount of cabergoline. The medicament may be in the form of tablet, powder mixture, capsule, solution, suspension, suppository, emulsion, dispersion or food premix. Preferably, the medicament is in the form of a tablet.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease is involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances. For example, a typical daily dose may contain from about 50 micrograms to about 150 mg of the active ingredient.

The present invention also discloses a new relatively stable solvate form of cabergoline, namely solvate form A of cabergoline. Solvate form A of cabergoline is a tert-butyl methyl ether solvate. Preferably, solvate form A of cabergoline is crystalline. In one embodiment, solvate form A of cabergoline is substantially pure. Suitably, solvate forms A of cabergoline contains not more than 20%, preferably not more than 10% of any other crystalline form of cabergoline. Most preferably the solvate form A of cabergoline contains not more than 5% of any other crystalline form of cabergoline.

The crystalline state of a compound can be unambiguously described by several crystallographic parameters: unit cell dimensions, space group, and atomic position of all atoms in the compound relative to the origin of its unit cell. These parameters are experimentally determined by single crystal x-ray analysis. The crystalline solvate form A of cabergoline is characterized by the crystal parameters obtained from single crystal x-ray crystallographic analysis set forth in Table 1 below.

TABLE 1

Crystal parameters of solvate form A of cabergoline.

| Formula | $C_{26}H_{37}N_5O_2 \cdot C_5H_{12}O$ |
|---|---|
| Formula weight (amu) | 539.75 |
| Space group | $P2_12_12_1$ |
| Cell dimensions | |
| a (Å) | 12.955 (3) |
| b (Å) | 14.312 (3) |
| c (Å) | 17.704 (4) |
| $\alpha = \beta = \gamma$ (°) | 90 |
| V (Å$^3$) | 3282.5 (13) |
| Z (molecules/units cell) | 4 |
| Density (g/cm$^3$) | 1.092 |

The unit cell dimension is defined by three parameters: length of the sides of the cell, relative angles of sides to each other and the volume of the cell. The lengths of the sides of the unit cell are defined by a, b and c. The relative angles of the cell sides are defined by α, β and γ. The volume of the cell is defined as V.

The crystalline solvate form A of cabergoline of the present invention is characterized by a single x-ray crystallographic analysis, which yields atomic positions of all atoms relative to the origin of the unit cell as shown in Tables 2 through 6, and as represented in FIG. 1. Tables 2 through 6 list the parameters of atomic coordinates, and their isotropic thermal parameters, bond lengths, bond angles, anisotropic thermal parameters, bond lengths, bond angles, anisotropic thermal parameters, and proton atom coordinates and their isotropic thermal parameters.

TABLE 2

Atomic coordinates (×10$^4$) and equivalent isotropic displacement parameters (Å$^2$ × 10$^3$). U (eq) is defined as one third of the trace of the orthogonalized Uij tensor.

| | x | y | z | U (eq) |
|---|---|---|---|---|
| N(1) | 4118(3) | 7929(3) | 4368(3) | 63(1) |
| C(2) | 4732(4) | 7161(4) | 4498(3) | 64(2) |
| C(3) | 5403(4) | 7341(4) | 5081(3) | 55(1) |
| C(4) | 6204(4) | 6784(3) | 5489(3) | 54(1) |
| C(5) | 6409(4) | 7215(3) | 6286(3) | 48(1) |
| N(6) | 7279(3) | 6750(3) | 6668(2) | 49(1) |
| C(7) | 7458(4) | 7167(4) | 7409(3) | 57(1) |
| C(8) | 7770(4) | 8178(4) | 7346(3) | 52(1) |
| C(9) | 6908(4) | 8727(3) | 6978(3) | 55(1) |
| C(10) | 6609(4) | 8297(3) | 6233(3) | 47(1) |
| C(11) | 5684(4) | 8779(3) | 5867(3) | 49(1) |
| C(12) | 5304(4) | 9663(4) | 5989(3) | 67(2) |
| C(13) | 4490(5) | 10015(4) | 5587(4) | 77(2) |
| C(14) | 4002(4) | 9515(4) | 5019(4) | 75(2) |
| C(15) | 4396(4) | 8630(4) | 4860(3) | 55(1) |
| C(16) | 5197(3) | 8277(4) | 5311(3) | 51(1) |
| C(17) | 7091(4) | 5741(3) | 6770(3) | 61(2) |
| C(18) | 7975(5) | 5242(4) | 7115(4) | 76(2) |
| C(19) | 7957(6) | 4754(5) | 7703(5) | 102(3) |
| C(20) | 8063(4) | 8581(4) | 8100(4) | 63(2) |
| O(21) | 7864(5) | 8156(3) | 8688(3) | 101(2) |
| N(22) | 8497(3) | 9456(3) | 8130(3) | 64(1) |
| C(23) | 8964(4) | 9914(5) | 7510(4) | 67(2) |
| O(24) | 9405(3) | 9454(3) | 7014(3) | 90(2) |
| N(25) | 8854(4) | 10832(4) | 7523(3) | 78(2) |
| C(26) | 9325(6) | 11395(5) | 6924(5) | 103(2) |
| C(27) | 9387(7) | 12381(5) | 7126(6) | 130(3) |
| C(28) | 8642(7) | 9881(5) | 8895(4) | 95(2) |
| C(29) | 7621(9) | 10132(5) | 9266(4) | 118(3) |
| C(30) | 7230(17) | 10991(13) | 9095(12) | 460(20) |
| N(31) | 7204(4) | 11472(4) | 8426(3) | 92(2) |
| C(32) | 6361(10) | 11310(20) | 7990(12) | 450(20) |
| C(33) | 7198(10 | 12430(7) | 8617(10) | 240(9) |
| C(34) | 4107(10) | 8272(7) | 9417(7) | 147(4) |
| C(35) | 4494(13) | 8563(9) | 8612(7) | 212(7) |
| C(36) | 4843(13) | 7794(11) | 9895(9) | 244(8) |
| C(37) | 3138(17) | 7644(16) | 9342(10) | 358(16) |
| O(38) | 3866(12) | 9146(8) | 9644(9) | 269(6) |
| C(39) | 3493(13) | 9134(17) | 10410(8) | 299(13) |

TABLE 3

Bond lengths (Å).

| N(1)—C(2) | 1.376(7) |
|---|---|
| N(1)—C(15) | 1.377(7) |
| N(1)—H(1) | 0.8600 |
| C(2)—C(3) | 1.373(7) |
| C(2)—H(2) | 0.9300 |
| C(3)—C(16) | 1.425(7) |
| C—(3)C(4) | 1.494(7) |
| C(4)—C(5) | 1.564(7) |
| C(4)—H(4A) | 0.9700 |
| C(4)—H(4B) | 0.9700 |

TABLE 3-continued

Bond lengths (Å).

| | |
|---|---|
| C(5)—N(6) | 1.472(6) |
| C(5)—C(10) | 1.574(7) |
| C(5)—H(5) | 0.93(5) |
| N(6)—C(7) | 1.460(6) |
| N(6)—C(17) | 1.476(6) |
| C(7)—C(8) | 1.506(7) |
| C(7)—H(7A) | 0.9700 |
| C(7)—H(7B) | 0.9700 |
| C(8)—C(20) | 1.503(7) |
| C(8)—C(9) | 1.513(7) |
| C(8)—H(8) | 0.96(5) |
| C(9)—C(10) | 1.507(7) |
| C(9)—H(9A) | 0.9700 |
| C(9)—H(9B) | 0.9700 |
| N(1)—C(2) | 1.376(7) |
| N(1)—C(15) | 1.377(7) |
| N(1)—H(1) | 0.8600 |
| C(2)—C(3) | 1.373(7) |
| C(10)—C(11) | 1.527(7) |
| C(10)—H(10) | 0.99(4) |
| C—(11)C(16) | 1.372(7) |
| C(11)—C(12) | 1.374(7) |
| C(12)—C(13) | 1.368(8) |
| C(12)—H(12) | 0.9300 |
| C(13)—C(14) | 1.387(8) |
| C(13)—H(13) | 0.9300 |
| C(14)—C(15) | 1.395(8) |
| C(14)—H(14) | 0.9300 |
| C(15)—C(16) | 1.404(7) |
| C(17)—C(18) | 1.481(8) |
| C(17)—H(17A) | 0.9700 |
| C(17)—H(17B) | 0.9700 |
| C(18)—C(19) | 1.253(9) |
| C(18)—H(18) | 0.9300 |
| C(19)—H(19A) | 0.9300 |
| C(19)—H(19B) | 0.9300 |
| C(20)—O(21) | 1.233(7) |
| C(20)—N(22) | 1.373(7) |
| N(22)—C(23) | 1.414(7) |
| N(22)—C(28) | 1.498(8) |
| C(23)—O(24) | 1.238(7) |
| C(23)—N(25) | 1.322(7) |
| N(25)—C(26) | 1.465(9) |
| C(26)—C(27) | 1.459(9) |
| C(26)—H(26A) | 0.9700 |
| C(26)—H(26B) | 0.9700 |
| C(27)—H(27A) | 0.9600 |
| C(27)—H(27B) | 0.9600 |
| C(27)—H(27C) | 0.9600 |
| C(28)—C(29) | 1.520(12) |
| C(28)—H(28A) | 0.9700 |
| C(28)—H(28B) | 0.9700 |
| C(29)—C(30) | 1.364(13) |
| C(29)—H(29A) | 0.9700 |
| C(29)—H(29B) | 0.9700 |
| C(30)—N(31) | 1.371(14) |
| C(30)—H(30A) | 0.9700 |
| C(30)—H(30B) | 0.9700 |
| N(31)—C(32) | 1.358(11) |
| N(31)—C(33) | 1.413(9) |
| N(31)—H(31) | 0.9100 |
| C(32)—H(32A) | 0.9600 |
| C(32)—H(32B) | 0.9600 |
| C(32)—H(32C) | 0.9600 |
| C(33)—H(33A) | 0.9600 |
| C(33)—H(33B) | 0.9600 |
| C(33)—H(33C) | 0.9600 |
| C(34)—O(38) | 1.350(14) |
| C(34)—C(36) | 1.446(15) |
| C(34)—C(37) | 1.550(17) |
| C(34)—C(35) | 1.568(16) |
| C(35)—H(35A) | 0.9600 |
| C(35)—H(35B) | 0.9600 |
| C(35)—H(35C) | 0.9600 |
| C(36)—H(36A) | 0.9600 |

TABLE 4

Bond Angles (°).

| | |
|---|---|
| C(2)—N(1)—C(15) | 109.0(4) |
| C(2)—N(1)—H(1) | 125.5 |
| C(15)—N(1)—H(1) | 125.5 |
| C(3)—C(2)—N(1) | 109.9(5) |
| C(3)—C(2)—H(2) | 125.0 |
| N(1)—C(2)—H(2) | 125.0 |
| C(2)—C(3)—C(16) | 105.9(4) |
| C(2)—C(3)—C(4) | 134.6(5) |
| C(16)—C(3)—C(4) | 119.5(5) |
| C(3)—C(4)—C(5) | 110.1(4) |
| C(3)—C(4)—H(4A) | 109.6 |
| C(5)—C(4)—H(4A) | 109.6 |
| C(3)—C(4)—H(4B) | 109.6 |
| C(5)—C(4)—H(4B) | 109.6 |
| H(4A)—C(4)—H(4B) | 108.1 |
| N(6)—C(5)—C(4) | 111.5(4) |
| N(6)—C(5)—C(10) | 110.3(4) |
| C(4)—C(5)—C(10) | 111.2(4) |
| N(6)—C(5)—H(5) | 109(3) |
| C(4)—C(5)—H(5) | 108(3) |
| C(10)—C(5)—H(5) | 107(3) |
| C(7)—N(6)—C(5) | 110.5(4) |
| C(7)—N(6)—C(17) | 108.4(4) |
| C(5)—N(6)—C(17) | 111.9(4) |
| N(6)—C(7)—C(8) | 111.6(4) |
| N(6)—C(7)—H(7A) | 109.3 |
| C(8)—C(7)—H(7A) | 109.3 |
| N(6)—C(7)—H(7B) | 109.3 |
| C(8)—C(7)—H(7B) | 109.3 |
| H(7A)—C(7)—H(7B) | 108.0 |
| C(20)—C(8)—C(7) | 111.8(5) |
| C(20)—C(8)—C(9) | 111.7(5) |
| C(7)—C(8)—C(9) | 109.5(4) |
| C(20)—C(8)—H(8) | 108(2) |
| C(7)—C(8)—H(8) | 115(2) |
| C(9)—C(8)—H(8) | 100(2) |
| C(10)—C(9)—C(8) | 110.8(4) |
| C(10)—C(9)—H(9A) | 109.5 |
| C(8)—C(9)—H(9A) | 109.5 |
| C(10)—C(9)—H(9B) | 109.5 |
| C(8)—C(9)—H(9B) | 109.5 |
| H(9A)—C(9)—H(9B) | 108.1 |
| C(9)—C(10)—C(11) | 112.9(4) |
| C(9)—C(10)—C(5) | 113.0(4) |
| C(11)—C(10)—C(5) | 109.9(4) |
| C(9)—C(10)—H(10) | 107(2) |
| C(11)—C(10)—H(10) | 108(2) |
| C(5)—C(10)—H(10) | 105(2) |
| C(16)—C(11)—C(12) | 115.5(5) |
| C(16)—C(11)—C(10) | 115.4(4) |
| C(12)—C(11)—C(10) | 129.1(5) |
| C(13)—C(12)—C(11) | 122.2(5) |
| C(13)—C(12)—H(12) | 118.9 |
| C(11)—C(12)—H(12) | 118.9 |
| C(12)—C(13)—C(14) | 122.6(5) |
| C(12)—C(13)—H(13) | 118.7 |
| C(14)—C(13)—H(13) | 118.7 |
| C(13)—C(14)—C(15) | 116.6(5) |
| C(13)—C(14)—H(14) | 121.7 |
| C(15)—C(14)—H(14) | 121.7 |
| N(1)—C(15)—C(14) | 134.0(5) |
| N(1)—C(15)—C(16) | 106.9(4) |
| C(14)—C(15)—C(16) | 118.9(5) |
| C(11)—C(16)—C(15) | 124.0(5) |
| C(11)—C(16)—C(3) | 127.7(5) |
| C(15)—C(16)—C(3) | 108.3(5) |
| N(6)—C(17)—C(18) | 113.3(5) |
| N(6)—C(17)—H(17A) | 108.9 |
| C(18)—C(17)—H(17A) | 108.9 |
| N(6)—C(17)—H(17B) | 108.9 |
| C(18)—C(17)—H(17B) | 108.9 |
| H(17A)—C(17)—(17B) | 107.7 |
| C(19)—C(18)—C(17) | 126.6(7) |
| C(19)—C(18)—H(18) | 116.7 |
| C(17)—C(18)—H(18) | 116.7 |
| C(18)—C(19)—H(19A) | 120.0 |
| C(18)—C(19)—H(19B) | 120.0 |

TABLE 4-continued

Bond Angles (°).

| | |
|---|---|
| H(19A)—C(19)—(19B) | 120.0 |
| O(21)—C(20)—N(22) | 120.2(5) |
| O(21)—C(20)—C(8) | 120.5(5) |
| N(22)—C(20)—C(8 | 119.2(5) |
| C(20)—N(22)—C(23) | 124.7(5) |
| C(20)—N(22)—C(28) | 117.1(5) |
| C(23)—N(22)—C(28) | 117.3(5) |
| O(24)—C(23)—N(25) | 126.2(6) |
| O(24)—C(23)—N(22) | 120.1(6) |
| N(25)—C(23)—N(22) | 113.7(6) |
| C(23)—N(25)—C(26) | 119.2(6) |
| C(27)—C(26)—N(25) | 112.1(7) |
| C(27)—C(26)—H(26A) | 109.2 |
| N(25)—C(26)—H(26A) | 109.2 |
| C(27)—C(26)—H(26B) | 109.2 |
| N(25)—C(26)—H(26B) | 109.2 |
| H(26A)—C(26)—H(26B) | 107.9 |
| C(26)—C(27)—H(27A) | 109.5 |
| C(26)—C(27)—H(27B) | 109.5 |
| H(27A)—C(27)—H(27B) | 109.5 |
| C(26)—C(27)—H(27C) | 109.5 |
| H(27A)—C(27)—H(27C) | 109.5 |
| H(27B)—C(27)—H(27C) | 109.5 |
| N(22)—C(28)—C(29) | 112.1(6) |
| N(22)—C(28)—H(28A) | 109.2 |
| C(29)—C(28)—H(28A) | 109.2 |
| N(22)—C(28)—H(28B) | 109.2 |
| C(29)—C(28)—H(28B) | 109.2 |
| H(28A)—C(28)—H(28B) | 107.9 |
| C(30)—C(29)—C(28) | 116.1(9) |
| C(30)—C(29)—H(29A) | 108.2 |
| C(28)—C(29)—H(29A) | 108.2 |
| C(30)—C(29)—H(29B) | 108.2 |
| C(28)—C(29)—H(29B) | 108.2 |
| H(29A)—C(29)—H(29B) | 107.4 |
| C(29)—C(30)—N(31) | 130.8(14) |
| C(29)—C(30)—H(30A) | 104.6 |
| N(31)—C(30)—H(30A) | 104.6 |
| C(29)—C(30)—H(30B) | 104.6 |
| N(31)—C(30)—H(30B) | 104.6 |
| H(30A)—C(30)—H(30B) | 105.7 |
| C(32)—N(31)—C(30) | 115.1(17) |
| C(32)—N(31)—C(33) | 107.4(14) |
| C(30)—N(31)—C(33) | 106.3(13) |
| C(32)—N(31)—H(31) | 109.3 |
| C(30)—N(31)—H(31) | 109.3 |
| C(33)—N(31)—H(31) | 109.3 |
| N(31)—C(32)—H(32A) | 109.1 |
| N(31)—C(32)—H(32B) | 110.3 |
| H(32A)—C(32)—H(32B) | 109.5 |
| N(31)—C(32)—H(32C) | 109.0 |
| H(32A)—C(32)—H(32C) | 109.5 |
| H(32B)—C(32)—H(32C) | 109.5 |
| N(31)—C(33)—H(33A) | 109.5 |
| N(31)—C(33)—H(33B) | 109.3 |
| H(33A)—C(33)—H(33B) | 109.5 |
| N(31)—C(33)—H(33C) | 109.6 |
| H(33A)—C(33)—H(33C) | 109.5 |
| H(33B)—C(33)—H(33C) | 109.5 |
| O(38)—C(34)—C(36) | 114.6(13) |
| O(38)—C(34)—C(37) | 112.0(15) |
| C(36)—C(34)—C(37) | 108.1(12) |
| O(38)—C(34)—C(35) | 95.6(10) |
| C(36)—C(34)—C(35) | 116.6(12) |
| C(37)—C(34)—C(35) | 109.5(12) |
| C(34)—C(35)—H(35A) | 109.5 |
| C(34)—C(35)—H(35B) | 109.4 |
| H(35A)—C(35)—H(35B) | 109.5 |
| C(34)—C(35)—H(35C) | 109.5 |
| H(35A)—C(35)—H(35C) | 109.5 |
| H(35B)—C(35)—H(35C) | 109.5 |
| C(34)—C(36)—H(36A) | 109.5 |
| C(34)—C(36)—H(36B) | 109.4 |
| H(36A)—C(36)—H(36B) | 109.5 |
| C(34)—C(36)—H(36C) | 109.5 |
| H(36A)—C(36)—H(36C) | 109.5 |
| H(36B)—C(36)—H(36C) | 109.5 |

TABLE 4-continued

Bond Angles (°).

| | |
|---|---|
| C(34)—C(37)—H(37A) | 109.6 |
| C(34)—C(37)—H(37B) | 109.5 |
| H(37A)—C(37)—H(37B) | 109.5 |
| C(34)—C(37)—H(37C) | 109.4 |
| H(37A)—C(37)—H(37C) | 109.5 |
| H(37B)—C(37)—H(37C) | 109.5 |
| C(34)—O(38)—C(39) | 110.3(13) |
| O(38)—C(39)—H(39A) | 109.5 |
| O(38)—C(39)—H(39B) | 109.5 |
| H(39A)—C(39)—H(39B) | 109.5 |
| O(38)—C(39)—H(39C) | 109.5 |
| H(39A)—C(39)—H(39C) | 109.5 |
| H(39B)—C(39)—H(39C) | 109.5 |

TABLE 5

Anisotropic displacement parameters ($Å^2 \times 10^3$).

| | $U_{33}$ | $U_{23}$ | $U_{13}$ | $U_{12}$ | $U_{11}$ | $U_{22}$ |
|---|---|---|---|---|---|---|
| N(1) | 45(2) | 74(3) | 71(3) | 1(3) | −18(2) | −8(2) |
| C(2) | 47(3) | 69(3) | 75(4) | −8(3) | −8(3) | −12(3) |
| C(3) | 41(3) | 60(3) | 63(4) | 0(3) | 0(3) | −7(2) |
| C(4) | 49(3) | 53(3) | 61(3) | −7(3) | −5(3) | −7(2) |
| C(5) | 35(3) | 54(3) | 56(3) | 0(3) | 9(3) | −9(2) |
| N(6) | 40(2) | 2(2) | 2(2) | −3(2) | 58(3) | 50(2) |
| C(7) | 45(3) | 67(4) | 58(3) | −2(3) | −17(3) | −2(2) |
| C(8) | 44(3) | 63(3) | 49(3) | 0(3) | −4(3) | −9(3) |
| C(9) | 52(3) | 53(3) | 61(4) | −10(3) | −5(3) | −4(2) |
| C(10) | 37(3) | 52(3) | 53(3) | 0(2) | 4(3) | −6(2) |
| C(11) | 40(3) | 55(3) | 53(3) | 5(3) | −3(3) | −6(2) |
| C(12) | 56(3) | 67(4) | 79(4) | −18(3) | −13(3) | 6(3) |
| C(13) | 84(4) | 63(4) | 85(5) | −2(3) | −16(4) | 16(3) |
| C(14) | 60(4) | 80(4) | 85(5) | 3(3) | −24(4) | 14(3) |
| C(15) | 39(3) | 67(3) | 60(3) | 2(3) | 2(3) | −3(3) |
| C(16) | 30(2) | 66(3) | 57(3) | −12(3) | −4(3) | −2(2) |
| C(17) | 64(3) | 48(3) | 71(4) | −2(3) | −12(3) | −4(3) |
| C(18) | 80(4) | 67(4) | 82(5) | 2(4) | −14(4) | 16(3) |
| C(19) | 107(6) | 82(5) | 118(7) | 20(5) | −33(5) | 8(4) |
| C(20) | 67(4) | 63(4) | 59(4) | 0(3) | −16(3) | 6(3) |
| O(21) | 159(5) | 80(3) | 65(3) | 3(3) | −25(3) | −19(3) |
| N(22) | 58(3) | 70(3) | 64(3) | −17(3) | −12(3) | −1(2) |
| C(23) | 37(3) | 83(4) | 80(4) | −3(4) | 1(3) | −7(3) |
| O(24) | 63(3) | 87(3) | 121(4) | −38(3) | 29(3) | −11(2) |
| N(25) | 68(3) | 68(3) | 99(4) | −10(3) | 18(3) | −8(3) |
| C(26) | 98(5) | 87(5) | 125(6) | −18(5) | −19(4) | 18(5) |
| C(27) | 138(7) | 108(6) | 145(8) | −8(5) | 31(7) | −55(5 |
| C(28) | 121(6) | 97(5) | 66(4) | −1(4) | 20(5) | −30(4) |
| C(29) | 197(10) | 87(5) | 69(5) | −13(4) | 20(6) | −16(6) |
| C(30) | 490(30) | 275(19) | 620(40) | 270(30) | 510(40) | 260(20) |
| N(31) | 64(4) | 125(5) | 86(4) | −28(4) | 12(3) | 16(3) |
| C(32) | 97(8) | 830(50) | 410(30) | −440(30) | −94(14) | 163(17) |
| C(33) | 174(11) | 108(7) | 440(30 | −5(7) | 146(14) | −104(11) |
| C(34) | 176(10) | 99(6) | 167(11) | 35(7) | −37(9) | 23(7) |
| C(35) | 310(20) | 173(12) | 154(11) | 35(9) | 1(12) | 36(12) |
| C(36) | 287(18) | 265(16) | 180(13) | 36(13) | −1(14) | 157(15) |
| C(37) | 380(30) | 450(30) | 240(20) | 150(20) | −130(20) | −270(30) |
| O(38) | 294(14) | 195(10) | 318(17) | 71(10) | −15(13) | 79(9) |
| C(39) | 226(16) | 520(30) | 150(12) | 135(17) | 100(13) | 107(19) |

TABLE 6

Hydrogen coordinates ($\times 10^4$) and isotropic displacement parameters ($Å^2 \times 10^3$).

| | x | y | z | U(eq) |
|---|---|---|---|---|
| H(1) | 3639 | 7965 | 4033 | 76 |
| H(2) | 4698 | 6602 | 4231 | 76 |
| H(4A) | 6839 | 6781 | 5198 | 65 |
| H(4B) | 5971 | 6144 | 5543 | 65 |
| H(7A) | 7998 | 6822 | 7667 | 68 |

TABLE 6-continued

Hydrogen coordinates (× 10⁴) and isotropic displacement parameters (Å² × 10³).

| | x | y | z | U(eq) |
|---|---|---|---|---|
| H(7B) | 6833 | 7120 | 7709 | 68 |
| H(9A) | 6313 | 8738 | 7310 | 66 |
| H(9B) | 7132 | 9366 | 6898 | 66 |
| H(12) | 5610 | 10034 | 6357 | 81 |
| H(13) | 4254 | 10613 | 5700 | 93 |
| H(14) | 3440 | 9758 | 4757 | 90 |
| H(17A) | 6942 | 5463 | 6282 | 73 |
| H(17B) | 6488 | 5657 | 7088 | 73 |
| H(18) | 8607 | 5296 | 6871 | 92 |
| H(19A) | 7342 | 4678 | 7968 | 123 |
| H(19B) | 8557 | 4468 | 7874 | 123 |
| H(26A) | 10014 | 11161 | 6822 | 124 |
| H(26B) | 8921 | 11329 | 6465 | 124 |
| H(27A) | 9579 | 12739 | 6690 | 196 |
| H(27B) | 9895 | 12464 | 7515 | 196 |
| H(27C) | 8727 | 12590 | 7307 | 196 |
| H(28A) | 9061 | 10440 | 8849 | 114 |
| H(28B) | 9011 | 9444 | 9216 | 114 |
| H(29A) | 7115 | 9664 | 9123 | 141 |
| H(29B) | 7709 | 10094 | 9809 | 141 |
| H(30A) | 7568 | 11412 | 9446 | 553 |
| H(30B) | 6515 | 10962 | 9256 | 553 |
| H(31) | 7785 | 11341 | 8157 | 110 |
| H(32A) | 6500 | 10789 | 7662 | 668 |
| H(32B) | 6199 | 11850 | 7693 | 668 |
| H(32C) | 5787 | 11160 | 8311 | 668 |
| H(33A) | 7251 | 12799 | 8166 | 361 |
| H(33B) | 7773 | 12563 | 8942 | 361 |
| H(33C) | 6567 | 12581 | 8874 | 361 |
| H(35A) | 4655 | 9218 | 8609 | 317 |
| H(35B) | 3963 | 8438 | 8247 | 317 |
| H(35C) | 5101 | 8211 | 8486 | 317 |
| H(36A) | 4569 | 7745 | 10398 | 366 |
| H(36B) | 5477 | 8141 | 9908 | 366 |
| H(36C) | 4971 | 7180 | 9698 | 366 |
| H(37A) | 2561 | 8016 | 9181 | 537 |
| H(37B) | 2985 | 7364 | 9821 | 537 |
| H(37C) | 3267 | 7163 | 8976 | 537 |
| H(39A) | 4068 | 9101 | 10751 | 448 |
| H(39B) | 3058 | 8599 | 10483 | 448 |
| H(39C) | 3106 | 9693 | 10507 | 448 |
| H(5) | 5810(40) | 7130(30) | 6580(30) | 48(13) |
| H(8) | 8320(30) | 8300(30) | 7000(30) | 38(12) |
| H(10) | 7210(30) | 8360(20) | 5890(20) | 30(10) |

Figure 2:
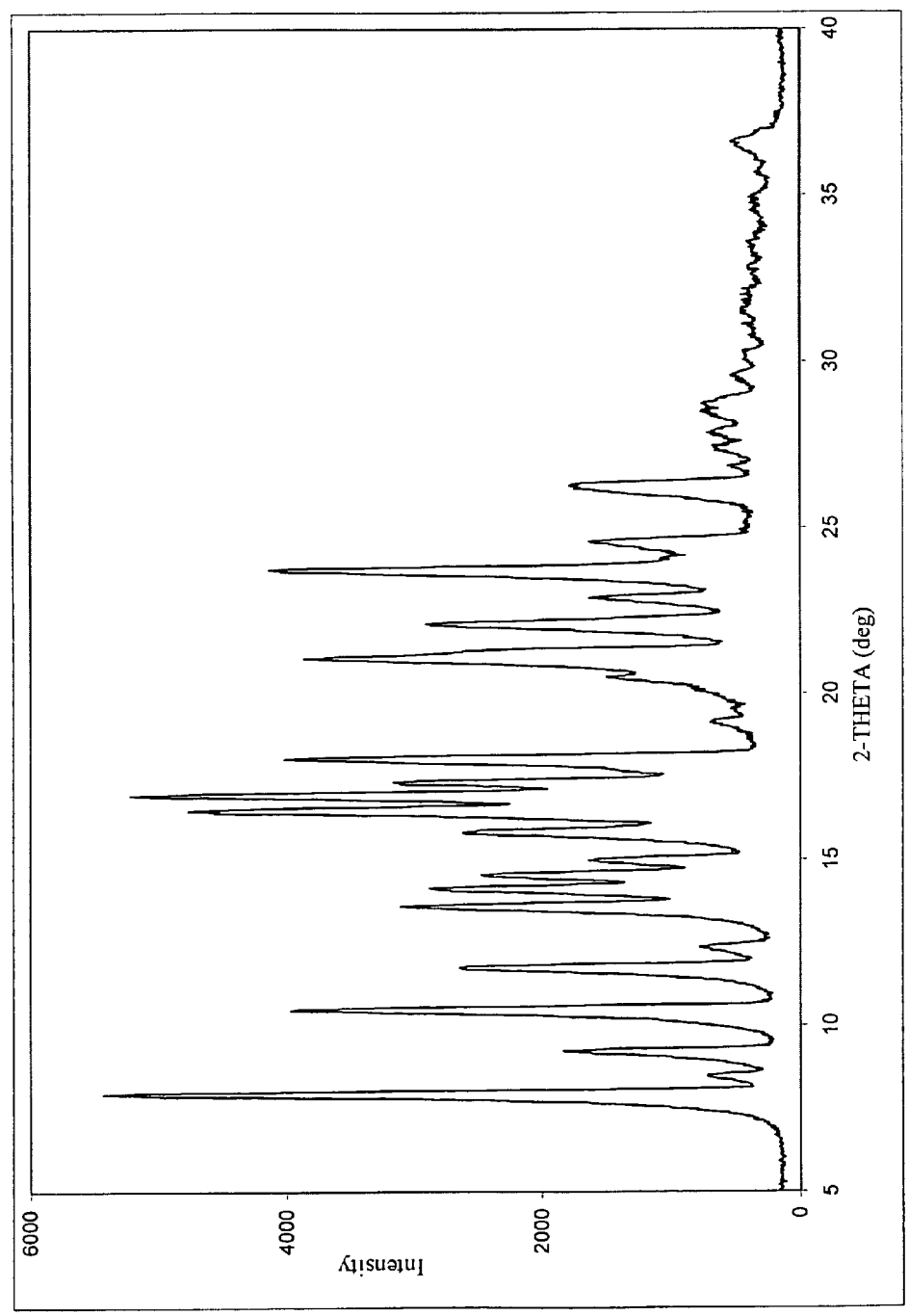
FIG. 2 shows a characteristic x-ray powder diffraction pattern of solvate form A of cabergoline. Vertical axis: intensity (CPS); Horizontal axis: 2θ (degrees).

Solvate form A of cabergoline also gives distinctive x-ray powder diffraction pattern, as depicted in FIG. 2. The pattern has characteristic peaks expressed in degrees 2θ at approximately 7.9±0.2, 10.5±0.2, 16.5±0.2, 17.0±0.2, 18.1±0.2 and 23.8±0.2.

The results of a single crystal x-ray analysis are limited to, as the name implies, one crystal placed in the x-ray beam. Crystallographic data on a large group of crystals provides powder x-ray diffraction. If the powder consists of a pure crystalline compound, a simple powder diagram is obtained. To compare the results of a single crystal analysis and a powder x-ray analysis, a simple calculation can be done converting the single crystal analysis and powder x-ray diagram. This conversion is possible because the single crystal experiment routinely determines the unit cell dimensions, space group, and atomic positions. These parameters provide a basis to calculate a perfect powder pattern.

In addition, comparison of the powder pattern experimentally obtained from a large collection of crystals to the calculated powder pattern of solvate form A of cabergoline shows correlation and similarity to each other. These results are graphically displayed in FIG. 2 and FIG. 3 and in Table 7.

TABLE 7

Calculated from single crystal X-ray analysis powder diffraction pattern (λ = 1.5418 Å radiation) where in I/I₁ represents the relative intensity:

| 2θ (°) | I/I₁ | h | k | l |
|---|---|---|---|---|
| 7.943 | 1000 | 0 | 1 | 1 |
| 8.457 | 141 | 1 | 0 | 1 |
| 9.207 | 213 | 1 | 1 | 0 |
| 10.478 | 650 | 1 | 1 | 1 |
| 11.755 | 332 | 0 | 1 | 2 |
| 12.369 | 62 | 0 | 2 | 0 |
| 13.603 | 401 | 1 | 1 | 2 |
| 13.670 | 62 | 2 | 0 | 0 |
| 14.139 | 317 | 1 | 2 | 0 |
| 14.561 | 342 | 2 | 0 | 1 |
| 15.002 | 139 | 1 | 2 | 1 |
| 15.830 | 228 | 2 | 1 | 1 |
| 15.925 | 95 | 0 | 2 | 2 |
| 16.506 | 533 | 1 | 0 | 3 |
| 16.961 | 593 | 2 | 0 | 2 |
| 17.343 | 361 | 1 | 2 | 2 |
| 18.066 | 521 | 2 | 1 | 2 |
| 20.462 | 129 | 1 | 3 | 1 |
| 21.046 | 278 | 2 | 2 | 2 |
| 21.155 | 53 | 0 | 3 | 2 |
| 21.292 | 319 | 2 | 1 | 3 |
| 22.079 | 89 | 3 | 1 | 1 |
| 22.113 | 165 | 1 | 1 | 4 |
| 22.252 | 133 | 1 | 3 | 2 |
| 22.913 | 170 | 3 | 0 | 2 |
| 23.753 | 539 | 3 | 1 | 2 |
| 23.889 | 72 | 2 | 2 | 3 |
| 24.597 | 124 | 3 | 2 | 1 |
| 24.628 | 84 | 1 | 2 | 4 |
| 26.119 | 57 | 3 | 2 | 2 |
| 26.320 | 236 | 3 | 1 | 3 |
| 27.403 | 59 | 2 | 2 | 4 |

Figure 3:
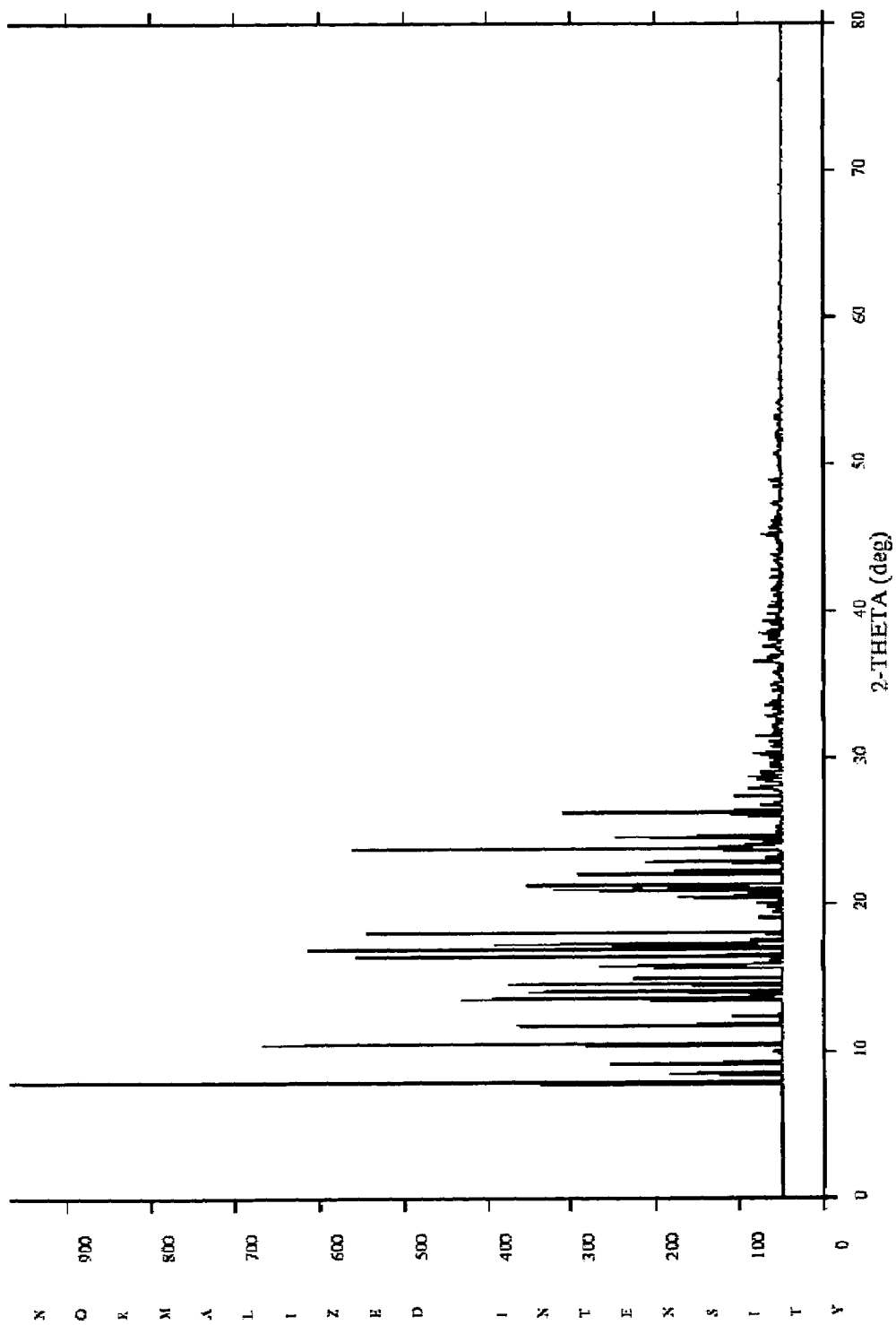
FIG. 3 shows calculated x-ray powder diffraction pattern of solvate form A cabergoline. Vertical axis: intensity (CPS); Horizontal axis: 2θ (degrees).

FIG. 2 shows an experimentally derived powder x-ray diffraction pattern of solvate form A of cabergoline and FIG. 3 corresponds to the x-ray diffraction derived from the single crystal x-ray data. The peak overlap indicates that the two techniques yield the same results. The primary powder x-ray diffraction peaks provide an unambiguous description of the crystalline state of solvate form A for cabergoline.

A pure crystalline organic compound has, in general, a definite melting point range. The melting point is defined as the point at which the sample is entirely in the liquid phase. The crystalline solvate form A of cabergoline has a characteristic melting point range determined by the capillary method from 66 to 70° C.

Figure 4:
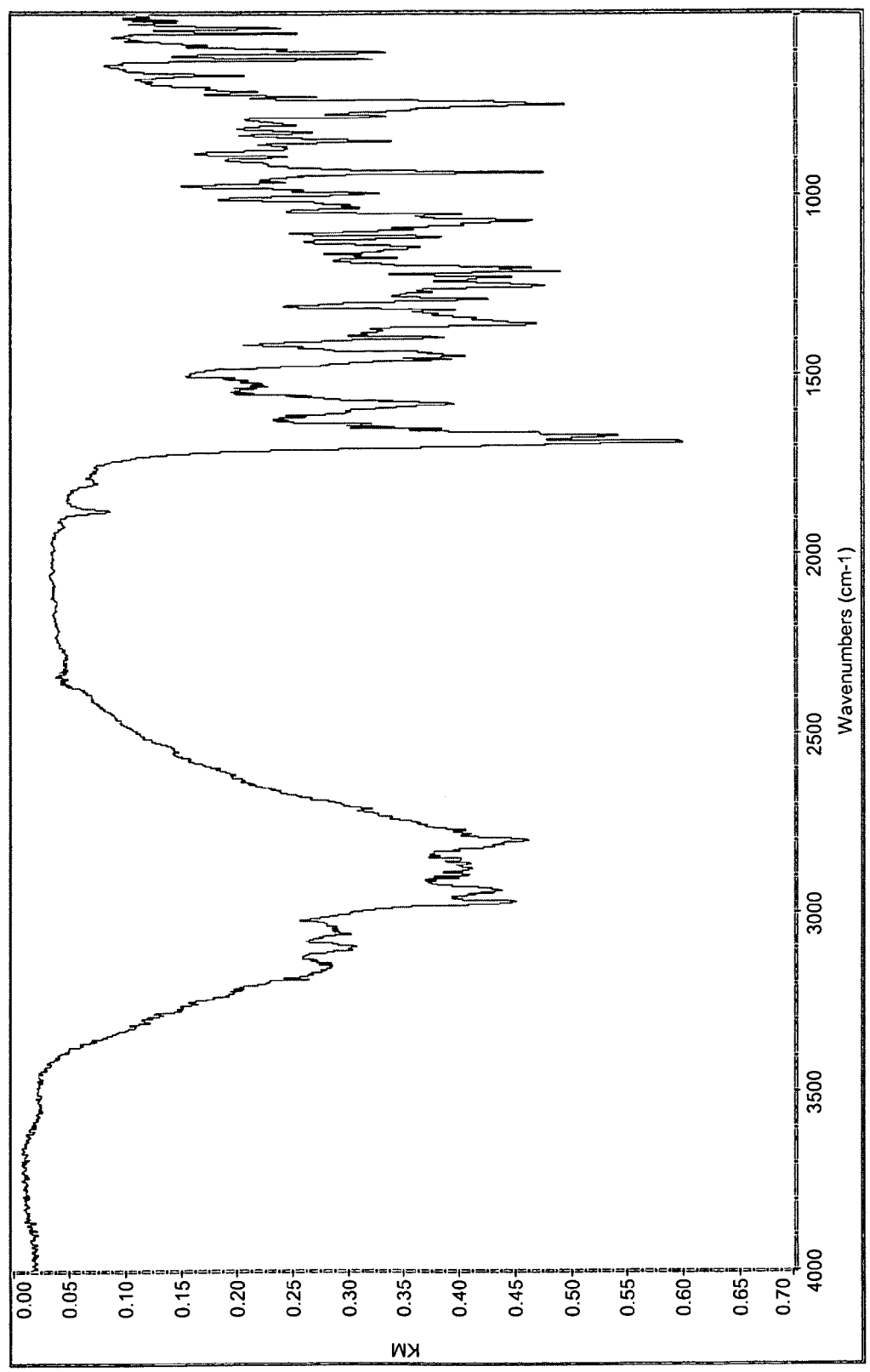
FIG. 4 shows the infrared spectrum (diffuse reflectance, DRIFTS) of solvate form A of cabergoline in potassium bromide.

The crystalline solvate form A of cabergoline was further characterized by an infrared absorption spectrum carried out in potassium bromide as depicted in FIG. 4.

Figure 5:
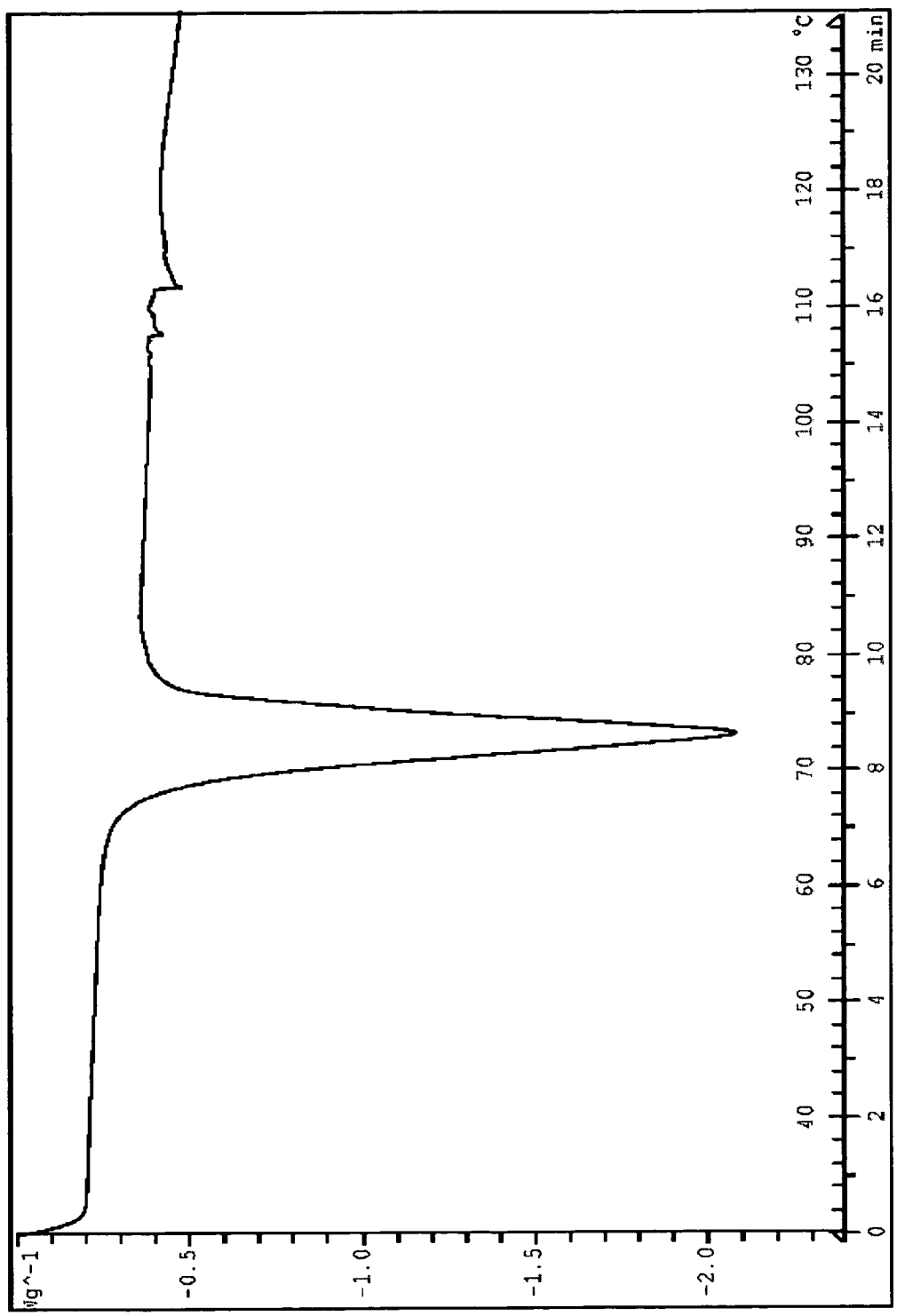
FIG. 5 shows the differential scanning calorimetry (DSC) curve of solvate form A of cabergoline, showing thermal event associated with eutectic melting of cabergoline with tert-buthyl methyl ether.

The DSC thermogram of solvate form A of cabergoline is shown in FIG. 5.

Figure 6:
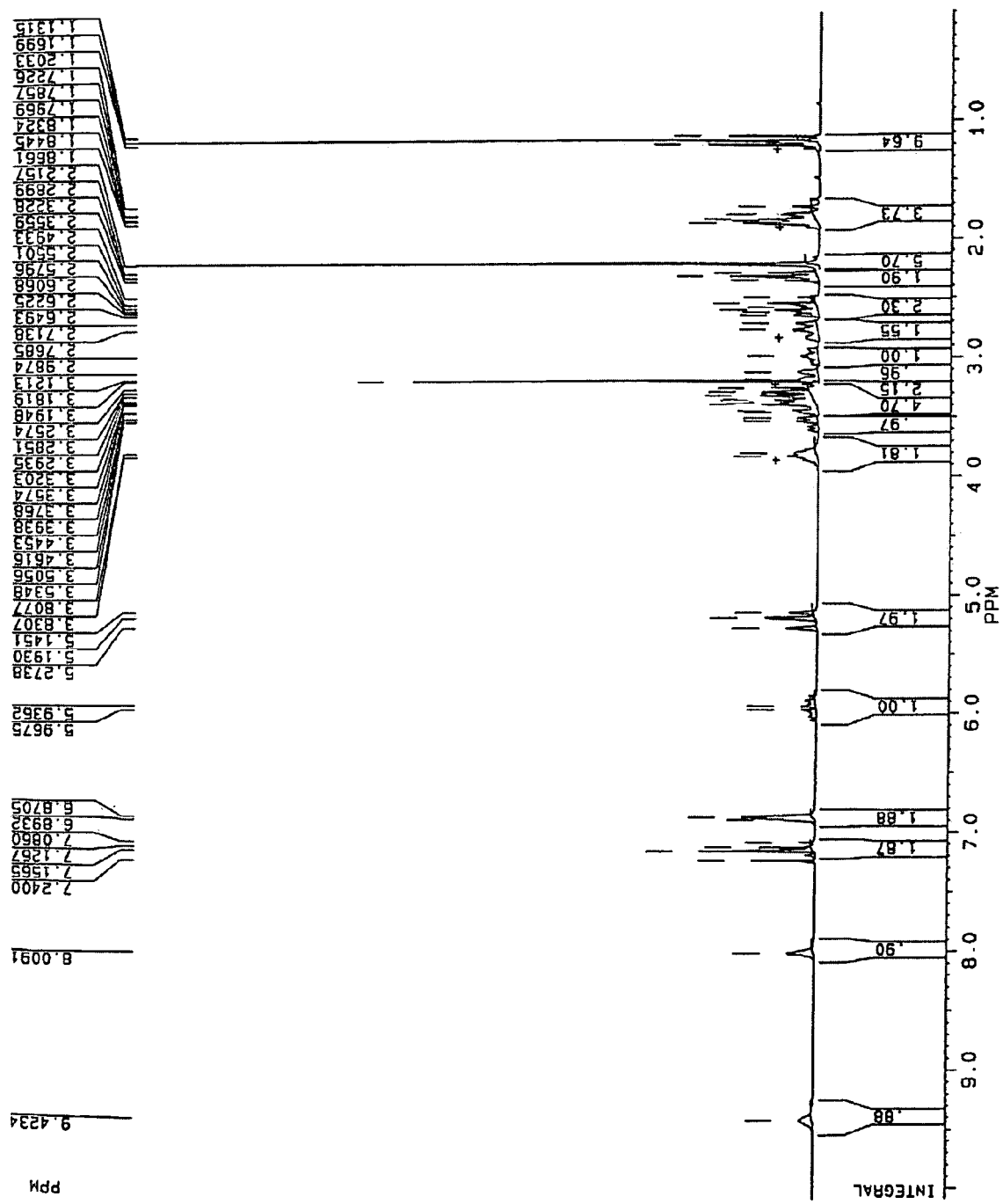
FIG. 6 shows the $^1$H nuclear magnetic resonance (NMR) spectrum of solvate form A of cabergoline in CDCl$_3$.

Solvate form A of cabergoline was further characterized by a ¹H magnetic resonance spectrum in CDCl₃ and shows characteristic absorption bands for the tert-butyl methyl ether moiety at approximately δ (ppm) 1.16 (singlet) and 3.18 (singlet). The ¹H NMR spectrum of solvate form A of cabergoline is shown in FIG. 6.

Crude non-crystalline cabergoline may be prepared by the method described in U.S. Pat. No. 6,696,568. Alternatively, crude non-crystalline cabergoline may be prepared by the methods described by Ashford (2002), Brambilla (1989), Candiani (1995), GB 2,103,603, U.S. Pat. No. 4,526,892 and U.S. Pat. No. 5,382,669. The present invention provides method for purifying of the crude cabergoline from related impurities comprising recrystallizing or crystallizing, or triturating or/and reslurring of the crude cabergoline in tert-butyl methyl ether. Preferably, the method for purifying of crude cabergoline from related impurities comprises the steps of:
a) recrystallizing or crystallizing, or triturating or/and reslurring of the crude solvate form A of cabergoline;
b) isolating the precipitated solid; and
c) drying the solid at 0–30° C. to obtain substantially pure solvate form A of cabergoline.

Alternatively, solvate form A of cabergoline also may be prepared by recrystallizing or crystallizing, or triturating or/and reslurring of any form of cabergoline in tert-butyl methyl ether.

Preferably, solvate form A of cabergoline may be prepared by:
a) mixing any physical form of cabergoline with tert-butyl methyl ether;
b) isolating the precipitated solid; and
c) drying the solid at 0–30° C. to obtain desired crystals.

The solvate form A of cabergoline prepared by the method of the invention may be used in the manufacture of pharmaceutical compositions, in a similar way as amorphous physical form of cabergoline. Thus, the present invention further provides the use of solvate form A of cabergoline in the manufacture of a medicament. Preferably, the medicament will be adapted for oral administration. Particularly suitable compositions for oral administration are unit dosage forms such as tablets and capsules.

The medicament may be prepared by combining the solvate form A of cabergoline with pharmaceutically acceptable excipients. Preferably, a method for preparing a pharmaceutical composition from solvate form A of cabergoline, comprising the step of combining an amount of solvate form A of cabergoline, an amount of a granulating fluid, and an amount of pharmaceutically acceptable excipient. More preferably, the method for preparing a pharmaceutical composition from solvate form A of cabergoline comprises the step of:
a) combining an amount of solvate form A of cabergoline, an amount of a granulating fluid, and an amount of pharmaceutically acceptable excipient;
b) blending to form a wet granulate; and
c) drying to obtain dry granules.

Most preferably, the method for preparing a pharmaceutical composition from solvate form A of cabergoline comprises the step of dissolving the solvate form A of cabergoline in the granulating fluid.

Preferably, the granulating fluid is water, organic solvent or combinations thereof. More preferably, the granulating fluid is ethanol, isopropanol or acetone. The excipient may be an acid, a carrier, a binder, a diluent, a lubricant, a glidant, an adjuvant or a combination thereof. Preferably, the acid is pharmaceutically acceptable organic or inorganic acid. More preferably, the acid is carboxylic acid, amino acid or combination thereof.

EXAMPLES

A better understanding of the present invention and of its many advantages will be had from the following non-limiting examples, given by way of illustration.

Experimental Details:

HPLC was carried out on a Merck-Hitachi Lachrom chromatographic system with UV detector.

Single crystal x-ray crystallographic analysis was performed on a Phillips PW 11000 diffractometer, ω/2θ mode, graphite monochromator, MoK$_\alpha$ radiation.

Powder x-ray diffraction patterns were obtained by methods known in the art using PANALYTICAL (Philips) X'Pert Pro MPD x-ray powder diffraction system (CuK$_\alpha$ radiation, PW3050/60 goniometer, PW3011/20 proportional detector). The Bragg-Brentano scheme was used for beam focusing.

$^1$H spectra were recorded on a Bruker AM-200 (200 MHz) and Bruker AM-400 (400 MHz) instruments using CDCl$_3$ as a solvent.

Melting points were determined in open capillary tubes with Buchi B-545 capillary melting point apparatus and are uncorrected. The melting points of solvent form A of cabergoline generally depend upon their level of purity. Typically, solvent form A of cabergoline has been found to have a melting point between 66 and 70° C.

Infrared absorption spectra were obtained with a Nicolet Impact 410 FT-IR spectrophotometer equipped with Pike Technologies EasiDiff Diffuse Reflectance Accessory using a 5% dispersion of sample material in a potassium bromide over the wave number range 400 to 4000 cm$^{-1}$.

DSC graphs were recorded on a Mettler DSC 30 Differential Scanning Calorimeter.

Example 1

Solvate Form A of Cabergoline

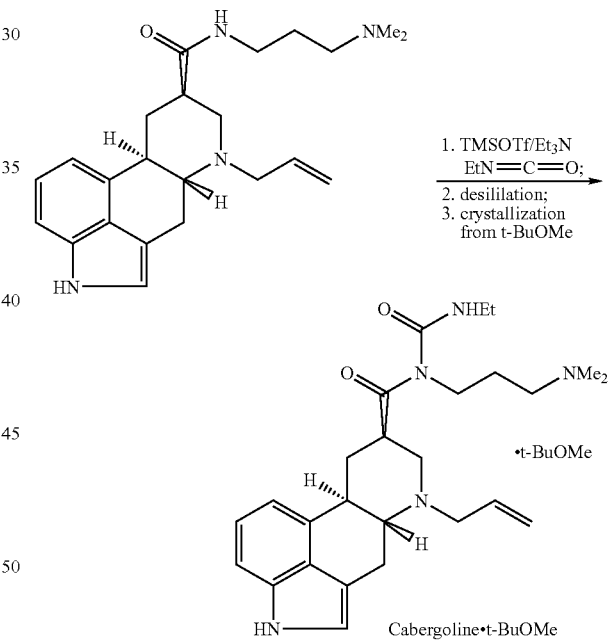

Trimethylsilyl trifluromethanesulfonate (7.6 g, 34.2 mmol, 1.1 eq) was added dropwise during 2 hours to a stirred mixture of N-[3-(dimethylamino)propyl]-6-allylergoline-8β-carboxamide (11.9 g, 31.5 mmol, 1 eq), triethylamine (3.8 g, 37.6 mmol, 1.2 eq) and dichloromethane (280 g) at −2° C. The mixture was stirred for 14 hours at 18° C. Ethyl isocyanate (11.1 g, 156.2 mmol, 5 eq) was added in one portion to the stirred mixture at 18° C. The obtained mixture was stirred for 48 hours at the same temperature. Tetrabutylammonium fluoride, 1.0 M solution in THF (30.4 g, 34.2 mmol, 1.1 eq) was added dropwise during 2 hours to the stirred mixture at −2° C. The reaction mixture was stirred for 2 hours at the same temperature and evaporated under reduced pressure. A solution of the residue in tert-butyl methyl ether was washed with aqueous solution of sodium bicarbonate and aqueous solution of sodium chloride, dried over sodium sulfate and passed through short silica gel column. The column was washed with acetone and the acetone solution was evaporated under reduced pressure to give 9.6 g (68.2%) of cabergoline as amorphous solid with 98% purity by HPLC. A hot solution of the amorphous cabergoline in tert-butyl methyl ether was kept at 0–5° C. for 60 hours. The precipitated solid was filtered off, washed on the filter with cold tert-butyl methyl ether and dried under reduced pressure at 15–25° C. to give 8.5 g (50%) solvate form A of cabergoline as white crystals with mp 66–70° C. and 99.8% purity by HPLC.

Solvate form A of cabergoline was characterized by powder x-ray diffractometry and IR spectroscopy as set forth above and in FIGS. 2 and 4. Single crystal of solvate form A of cabergoline was isolated and used for determination crystallographic parameters (see Tables 1–6).

Example 2

Purification of Crude Cabergoline

Crude cabergoline with 97–99% purity by HPLC, prepared according to Brambilla (1989), Candiani (1995) or Ashford (2002) was crystallized from tert-butyl methyl ether to give after drying under reduced pressure at 15–25° C. solvate form A of cabergoline as off-white crystals with purity of at least 99.5% by HPLC.

Example 3

Solvate Form A of Cabergoline

A mixture of cabergoline (2.0 g) and tert-butyl methyl ether (4.5 mL) was stirred for 3 days at 0–5° C. Precipitated crystals were filtered off, washed on the filter with cold tert-butyl methyl ether (4.5 mL) and dried under reduced pressure at 15–25° C. to give 1.8 g (88%) solvate form A of cabergoline as off-white crystals.

Example 4

Amorphous Physical Form of Cabergoline

A solution of solvate form A of cabergoline (5.0 g) in diethyl ether (67 mL) was added dropwise during 1 hour to a stirred pentane (130 mL) at −25° C. The resulted mixture was stirred for 3 hours at the same temperature. Precipitated solid were filtered off and dried under reduced pressure at 20–25° C. to give 3.5 g of amorphous physical form of cabergoline.

Example 5

Amorphous Physical Form of Cabergoline

A solution of solvate form A of cabergoline (196.6 g) in diethyl ether (2.7 L) was added dropwise during 5 hours to a stirred pentane (5.2 L) at −20° C. The resulted mixture was stirred for 3 hours at the same temperature and evaporated under reduced pressure to give 154.3 g of amorphous physical form of cabergoline.

The amorphous physical form of cabergoline was characterized by x-ray powder diffractometry and infrared spectroscopy (see FIGS. 7 and 8).

Example 6

Amorphous Physical Form of Cabergoline

A 6% solution of solvate form A of cabergoline in cyclohexane was lyophilized to give amorphous physical form of cabergoline.

Example 7

Amorphous Physical Form of Cabergoline

A solution of solvate form A of cabergoline in isopropanol was evaporated under reduced pressure at 45° C. to give amorphous physical form of cabergoline.

Example 8

Amorphous Physical Form of Cabergoline

A solution of solvate form A of cabergoline (1.0 g) in a mixture of acetic acid (2.5 g) and water (10 mL) was washed with heptane (5 mL) and added dropwise to a stirred 25% aqueous ammonia solution (5 mL) at 5–15° C. The resulting mixture was stirred for 0.5 hours at the same temperature. Precipitated solid was filtered off and dried under reduced pressure at 25–35° C. to give 0.6 g of amorphous physical form of cabergoline.

Example 9

Amorphous Physical Form of Cabergoline

A solution of solvate form A of cabergoline (1.0 g) in a mixture of acetic acid (2.5 g) and water (10 mL) was washed with heptane (5 mL). A 25% aqueous ammonia solution (5 mL) was added dropwise to the stirred solution of cabergoline at 5–15° C. The resulting mixture was stirred for 0.5 hours at the same temperature. Precipitated solid was filtered off and dried under reduced pressure at 25–35° C. to give 0.7 g of amorphous physical form of cab ergo line.

Example 10

Tablets Prepared from Amorphous Physical Form of Cabergoline

About one thousand tablets were compressed from the mixture of amorphous physical form of cabergoline (0.5 g), citric acid anhydrous (1.2 g), croscarmellose sodium (2.4 g), magnesium stearate (0.1 g) and microcrystalline cellulose (75.8 g).

Example 11

Tablets Prepared From Solvate Form A of Cabergoline

Granulate obtained by mixing of microcrystalline cellulose (75.1 g) and citric acid anhydrous (1.2 g) with a solution of solvate form A of cabergoline (0.6 g) in isopropanol was dried to give acceptable dry granules which were submitted to milling. The dried-milled granules were mixed with croscarmellose sodium (2.4 g) and with magnesium stearate (0.1 g). Finally, the lubricated blend was compressed to manufacture about one thousand tablets.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. Amorphous physical form of cabergoline substantially free of other physical forms, which is characterized by a halo x-ray powder diffraction pattern having a range of signals from between about 15 to about 23 degrees 2-theta.

2. Amorphous physical form of cabergoline which is characterized by an infrared spectrum having signals at about 3310, 3290, 2935, 1690, and 750 cm$^{-1}$.

3. A process for preparing amorphous physical form of cabergoline, comprising preparing a solvate form A of cabergoline which is characterized by an x-ray powder diffraction pattern of FIG. 2, and converting the solvate form A of cabergoline into an amorphous physical form of cabergoline.

4. The process according to claim 3 which further comprises the steps of:
a) dissolving solvate form A of cabergoline in an organic solvent; and b) evaporating the solution prepared in step (a) to obtain the amorphous physical form of cabergoline.

5. The process according to claim 3 which further comprises the steps of: a) dissolving form A of cabergoline in an organic solvent; b) mixing the solution of cabergoline with an anti-solvent; and c) isolating the amorphous physical form of cabergoline.

6. The process according to claim 3 which further comprises the steps of: a) dissolving form A of cabergoline in an aqueous acid; b) mixing the solution of cabergoline with an aqueous base; and c) isolating the precipitated amorphous physical form of cabergoline.

7. The process according to claims 4 or 5 wherein said organic solvent is selected from the group consisting of alcohols, ketones, esters and ethers.

8. The process according to claim 5, wherein said anti-solvent is a saturated hydrocarbon.

9. The process according to claim 8, wherein said anti-solvent is selected from the group consisting of pentane, heptane, hexane and cyclohexane.

10. The process according to claim 4 which further comprises the step of drying the amorphous physical form of cabergoline under reduced pressure at 0–40° C.

11. A process for preparing amorphous physical form of cabergoline, comprising the steps of: a) dissolving solvate form A of cabergoline which is characterized by an x-ray powder diffraction pattern of FIG. 2, in a solvent; and b) lyophilizing the solution prepared in step (a) to obtain the amorphous physical form of cabergoline.

12. The process according to claim 11 wherein said solvent is selected from the group consisting of tert-butanol, aqueous tert-butanol, 1,4-dioxane, aqueous 1,4-dioxane, benzene, dimethyl carbonate and cyclohexane.

13. The amorphous physical form of cabergoline according to claim 1 which is characterized by an x-ray powder diffraction pattern as shown in FIG. 7.

14. The amorphous physical form of cabergoline according to claim 2, which is characterized by an infrared spectrum as shown in FIG. 8.

* * * * *